United States Patent [19]

Choumei

[11] Patent Number: 5,225,891
[45] Date of Patent: Jul. 6, 1993

[54] WIRE BONDING EXTERNAL APPEARANCE INSPECTING APPARATUS

[75] Inventor: Masayuki Choumei, Ito, Japan

[73] Assignee: Kabushiki Kaisha Toshiba, Kawasaki, Japan

[21] Appl. No.: 771,970

[22] Filed: Oct. 9, 1991

[30] Foreign Application Priority Data

Oct. 9, 1990 [JP] Japan .................................. 2-271387

[51] Int. Cl.⁵ ...................... G01B 11/24; G01N 21/88
[52] U.S. Cl. ..................................... 356/376; 356/237; 356/394; 358/101; 358/106
[58] Field of Search ...................... 356/376, 394, 237; 250/560; 382/8; 358/101, 106

[56] References Cited

U.S. PATENT DOCUMENTS 5,030,008  7/1991  Scott et al. ........................... 356/394

FOREIGN PATENT DOCUMENTS

| | | | |
|---|---|---|---|
| 155802 | 12/1981 | Japan | 356/376 |
| 8705 | 1/1985 | Japan | 356/237 |
| 307309 | 12/1988 | Japan | 356/237 |
| 276004 | 11/1989 | Japan | 356/237 |
| 140606 | 5/1990 | Japan | 356/376 |
| WO91/12489 | 8/1991 | PCT Int'l Appl. | 356/237 |

*Primary Examiner*—F. L. Evans
*Attorney, Agent, or Firm*—Foley & Lardner

[57] ABSTRACT

A wire bonding external appearance inspecting apparatus for inspecting wires bonded to a semiconductor chip and the vicinity thereof, comprises a plurality of illuminating units of different illumination directions, for illuminating the semiconductor chip and the vicinity thereof, and a controller for selecting and operating any one of the plural illuminating units according to the inspection places thereof. Since an optimum illumination can be obtained according to inspection items, a camera can take plural different images according to objects to be inspected, so that the inspection reliability can be improved.

4 Claims, 3 Drawing Sheets

WIRE BONDING EXTERNAL APPEARANCE INSPECTING APPARATUS

BACKGROUND OF THE INVENTION

The present invention relates to an apparatus for inspecting the external appearance of wire bonding between a semiconductor chip and leads.

After wire bonding between a semiconductor chip and leads has been completed, it is necessary to inspect whether wires are bonded at their correct positions, in straight lines without being curved, not disconnected, etc. These external appearance inspections can be carried out by automatically processing an image obtained by a camera.

During inspection, it is necessary to illuminate the semiconductor chip, wires, and leads to be inspected. In the prior-art inspection, these objects to be inspected have been illuminated as shown in FIG. 4. In the drawing, a bed 13 of a lead frame 18 is supported by tie bars 15, and semiconductor chips 11 are mounted on this bed 13. Wires 17 are connected between electrodes 11a of the semiconductor chip 11 and leads 14 arranged near the bed 13 as shown.

These objects to be inspected are imaged by a camera 21 disposed thereover under illumination of a downward illuminating means 2 disposed in the vicinity of the camera 21 for illuminating the objects from above.

In the prior-art apparatus, however, since only a single illuminating means is provided, the illumination direction is limited to one direction, thus causing a problem in that the illumination intensity is not sufficient, for each of the items to be inspected and therefore the inspection reliability is inevitably degraded. In more detail, there are some inspection items such as the detection of the position of a reference mark 12 representative of a reference position used to determine the coordinates of the semiconductor chip 11, the detection of the position of another reference mark 16 representative of a reference position of a lead frame 18, the inspection of shapes of the leads 14, the inspection of shapes of the bonded wires 17, etc.

In each of these inspections, the optimum illumination direction differs. For instance, when the position of the reference mark 12 is required to be detected, it is preferable to illuminate the semiconductor chip 11 from above. When inspecting other items, however, this illumination direction is not preferable and therefore a satisfactory image cannot be obtained. Where a high quality image cannot be obtained by the camera 21 for inspection purposes, there exists a problem in that the inspection reliability is degraded and therefore a sufficient guarantee for the product quality cannot be achieved. In addition, where the inspection is made on the basis of a dissatisfactory image, there exists a problem in that a long image processing time is required, thus increasing the inspection cost.

SUMMARY OF THE INVENTION

Accordingly, an object of the present invention is to provide a wire bonding external appearance inspecting apparatus by which optimum illumination directions can be selected according to which items are to be inspected.

To achieve the above-mentioned object, the wire bonding external appearance inspecting apparatus for inspecting external appearances of wires bonded to a semiconductor chip and the vicinity thereof according to the present invention is includes a plurality of illuminating means of different illumination directions, for illuminating the semiconductor chip and the vicinity thereof; and control means for selecting any of said plural illuminating means according to inspection places and controlling operation thereof.

During the inspection, the illumination direction differs according to the item to be inspected, such as the position of the semiconductor chip, the positions and shapes of the leads, the shapes of the wires, etc. Therefore, a plurality of illuminating means of different illumination directions are provided, and the operation of the illuminating means is controlled according to the items being inspected in order to obtain the optimum illumination, and improve the inspection reliability.

In the inventive apparatus first illuminating means for illuminating the semiconductor chip from above, second illuminating means for illuminating the same from below, and third illuminating means for illuminating the same from the side are provided as the plural illuminating means thus, one illumination direction to the semiconductor chip can be selected from the above three directions, so that it is possible to illuminate the semiconductor chip from the optimum direction according to the inspection places.

The first, second and third illuminating means are connected to first, second and third power sources, respectively, and further the control means selects and operates any one of the three illuminating means by controlling the on-off operation of the three power sources thus, any one of the power sources can be turned on by the control means to supply power to the corresponding illuminating means.

BRIEF DESCRIPTION OF THE DRAWINGS

In the attached drawings.

DESCRIPTION OF THE PREFERRED EMBODIMENTS

Figure 1:
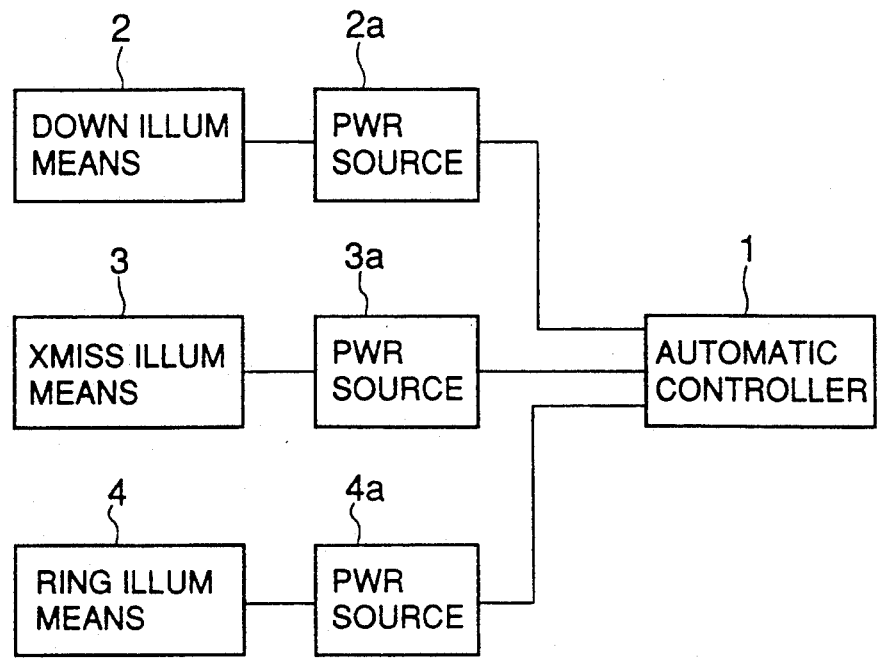
FIG. 1 is a block diagram showing the organization of an embodiment of the wire bonding external appearance inspecting apparatus according to the present invention.

An embodiment of the present invention will be described hereinbelow with reference to the drawings. FIG. 1 is a block diagram of the embodiment of the wire bonding external appearance inspecting apparatus. The inspecting apparatus is provided with downward illuminating means 2, transmissible illuminating means 3 and ring illuminating means 4. The illuminating means 2, 3 and 4 are connected to three power sources 2a, 3a and 4a, respectively. Further, these power sources 2a, 3a and 4a are connected to an automatic controller 1. The on-off operation of the respective power sources 2a, 3a and 4a is controlled automatically according to the items to be inspected by the automatic controller 1.

Figure 2:
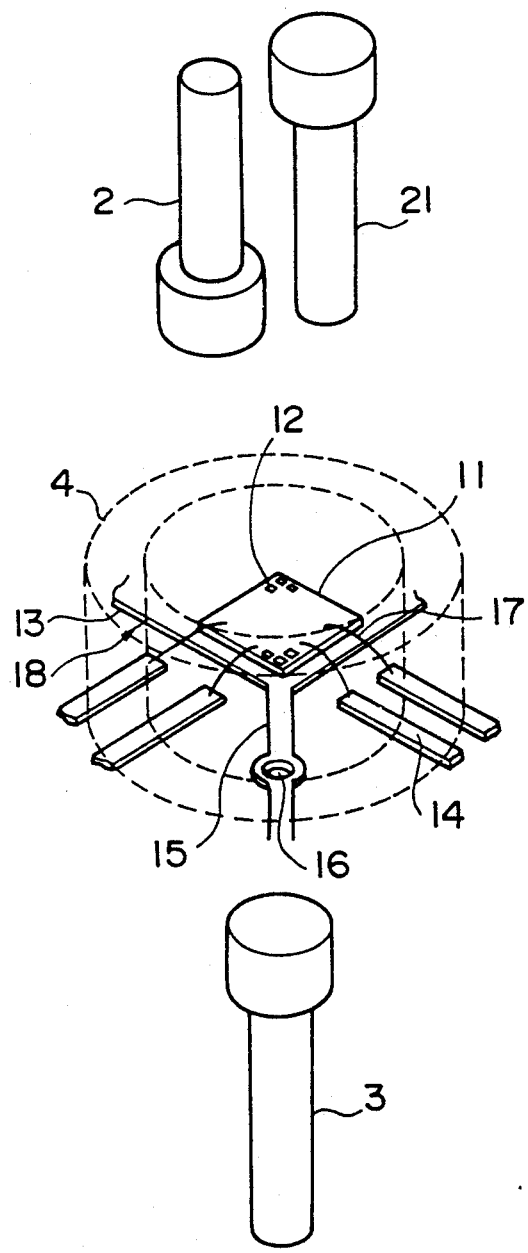
FIG. 2 is a perspective view showing the arrangement of illuminating means of the same inspecting apparatus.
Figure 4:
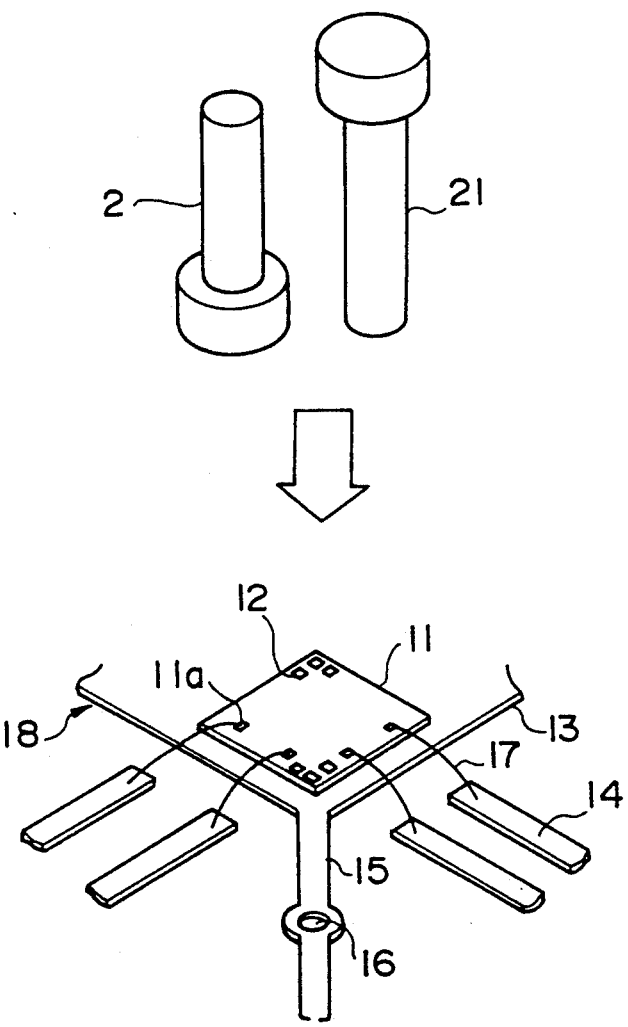
FIG. 4 is a perspective view showing a prior-art wire bonding external appearance inspecting apparatus.

The illuminating means 2, 3, 4 are arranged as shown in FIG. 2. In the same way as discussed for FIG. 4, wires 17 are bonded between a semiconductor chip 11 mounted on a bed 13 and leads. A camera 21 for picking up or taking an image of the wires 17 to be inspected is positioned over the semiconductor chip 11. The illuminating means 2, 3, 4 are arranged in the vicinity of the object to be inspected. The downward illuminating means 2 is located over the semiconductor chip 11; the transmissible illumination means 3 is located under the semiconductor chip 11; and the ring illuminating means 4 of annular shape is located so as to enclose the periphery of the semiconductor chip 11.

The downward illuminating means 2 is used to detect a reference mark 12 on the semiconductor chip 11. The upper surface of the reference mark 12 is finished into a mirror surface state. Therefore, when the downward illuminating means 2 illuminates the reference mark 12 from above, the light is reflected upward from the reference mark 12 to the camera 21. On the other hand, since the other surface of the semiconductor chip 11 is finished rather roughly, the illumination light irradiated thereupon is reflected in a diffused manner. The camera 21 is disposed over the semiconductor chip 11 and the downward illuminating means 2 is disposed over the reference mark 12. The optical axis of the camera 21 is in the same direction as the illumination direction of the downward illuminating means 2. Therefore, the camera 21 can accurately detect the position of the reference mark 12 because the reference mark 12 is recognized as being bright while the remaining surface area of the semiconductor chip 11 is recognized as being dark such that a clear difference in brightness between the two exists.

The transmissive illuminating means 3 is suitable for inspection of the reference mark 16 of the lead frame 18 or the shape of the leads 14. When the transmissible illuminating means 3 illuminates the semiconductor chip 11 from below, light is transmitted through the semiconductor chip 11 toward the camera 11, except the leads 14 formed of an Fe-Ni alloy. Therefore, since a hole is formed in the tie bar 15 as a reference mark 16, light is also transmitted through this reference hole 16. Accordingly, the locations of the leads 14 and the tie bar 15 (except the reference mark 16) can be recognized by the camera as clear shadow portions, so that it is possible to detect the position of the reference mark 16 and the presence or absence of curves in the leads 14.

Figure 3:
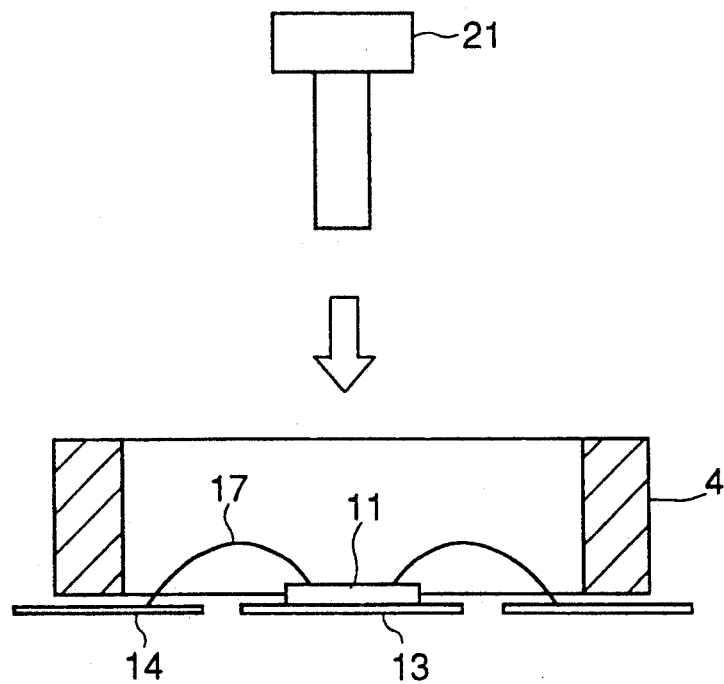
FIG. 3 is a cross-sectional view showing an arrangement of ring illuminating means of the same inspecting apparatus.

The ring illuminating means 4 is used to inspect the shapes of the wires 17. FIG. 3 shows the way of illuminating the wires 17 by the ring illuminating means 4. The semiconductor chip 11 located at the center of the ring illuminating means 4 is illuminated by light transmitted radially inward from the inner circumferential side surface of the ring illuminating means 4. Since there exist height difference between the wires 17, and the semiconductor chip 11 and the leads 14 as shown in FIG. 3, the illumination light transmitted from the ring illuminating means 4 is reflected from the wires 17 upward to the camera 21, and therefore the bright wires 17 are imaged by the camera 21. That is, it is possible to sufficiently recognize the curved conditions of the wires 17 on the basis of clear differences in brightness between the wires and the other portions.

As described above, the different illuminating means 2, 3, 4 are respectively used by sending on the items to be inspected. The respective power sources 2a, 3a and 4a are controllably turned on or off by the automatic controller 1, so that the object to be inspected can be illuminated by an optimum illuminating means of the downward illuminating means 2, the transmissible illuminating means 3 and the ring illuminating means 4 depending on the items being inspected. Here, the procedures for the respective inspections are previously input into the automatic controller 1. Therefore, power supply from the respective power sources 2a, 3a and 4a to the respective illuminating means 2, 3 and 4 is automatically controlled according to the inspection items in accordance with the procedures input into the automatic controller 1.

As described above, according to the present embodiment, since three kinds of illuminating means are automatically and controllably selected and operated so that an optimum illumination can be obtained according to the items being inspected, it is possible for the camera 21 to sufficiently recognize the objects to be inspected. Therefore, it is possible to more clearly discriminate whether products are defective or non-defective, thus improving the inspection reliability. In addition, since the camera 21 can take a clear image, the image processing can be executed smoothly and the image processing speed can be increased, thus reducing the inspection cost.

What is claimed is:

1. A wire bonding external appearance inspecting apparatus for inspecting external appearances of an assembly having a lead frame including a first reference mark, a semiconductor chip having a second reference mark and being disposed on the lead frame, and wires extending from the semiconductor chip, the apparatus comprising:
   a first illuminator disposed above the assembly which illuminates the assembly from above;
   a second illuminator disposed below the assembly which illuminates the assembly from below;
   a third illuminator disposed lateral to the assembly which illuminates the assembly from its side; and
   control means for selecting and illuminating a single one of the first, second and third illuminators such that the first illuminator is illuminated when the second reference mark is being inspected, the second illuminator is illuminated when at least one of the first reference mark and a shape of the lead frame is being inspected, and the third illuminator is illuminated when shapes of the wires are being inspected.

2. An apparatus as recited in claim 1, further comprising first, second and third power sources connected to the first, second and third illuminators respectively, and wherein the control means selects and illuminates a single one of the first, second and third illuminators by controlling an on-off operation of each of the first, second and third power sources, respectively.

3. A method for inspecting comprising the steps of:
   a) providing an assembly including a semiconductor chip having a first reference mark thereon, a lead frame upon which the semiconductor chip is disposed, and wires extending from the semiconductor chip, the lead frame having a second reference mark thereon;
   b) only illuminating the assembly from above when inspecting the first reference mark;
   c) only illuminating the assembly from below when inspecting at least one of the second reference mark and a shape of the lead frame;
   d) only illuminating the assembly from the side when inspecting shapes of the wires,
   e) creating an image of the first reference mark during step b);

f) creating an image of the at least one of the second reference mark and the shape of the lead frame during step c); and g) creating an image of the shape of the wires during step d).

4. A method as recited in claim 2, further comprising identifying which of the first reference mark, the at least one of the second reference mark and the shape of the lead frame, and the shapes of the wires is to be inspected, and selecting which of steps b), c) and d) is to be performed based on the identifying step.

* * * * *